US010261057B2

(12) United States Patent
Gebauer et al.

(10) Patent No.: US 10,261,057 B2
(45) Date of Patent: Apr. 16, 2019

(54) STACKABLE CHROMATOGRAPHY COLUMN MODULES AND FLOW CONTROL BLOCKS

(71) Applicant: GE Healthcare Bio-Sciences AB, Uppsala (SE)

(72) Inventors: Klaus Gebauer, Uppsala (SE); Mats Lundkvist, Uppsala (SE); Bjorn Olovsson, Uppsala (SE)

(73) Assignee: GE Healthcare BioProcess R&D AB, Uppsala (SE)

( * ) Notice: Subject to any disclaimer, the term of this patent is extended or adjusted under 35 U.S.C. 154(b) by 136 days.

(21) Appl. No.: 15/329,199

(22) PCT Filed: Jul. 6, 2015

(86) PCT No.: PCT/EP2015/065311
§ 371 (c)(1),
(2) Date: Jan. 25, 2017

(87) PCT Pub. No.: WO2016/015952
PCT Pub. Date: Feb. 4, 2016

(65) Prior Publication Data
US 2017/0219541 A1    Aug. 3, 2017

(30) Foreign Application Priority Data
Jul. 28, 2014 (SE) ...................................... 1450916

(51) Int. Cl.
*G01N 30/60* (2006.01)
*G01N 30/46* (2006.01)
(Continued)

(52) U.S. Cl.
CPC ..... *G01N 30/6039* (2013.01); *B01D 15/1864* (2013.01); *G01N 30/465* (2013.01);
(Continued)

(58) Field of Classification Search
CPC ......... B01L 2400/0644; F16K 99/0013; G01N 30/466; G01N 30/461; G01N 30/02
See application file for complete search history.

(56) References Cited

U.S. PATENT DOCUMENTS 3,496,960 A * 2/1970 Hughes .................. F04C 28/02
137/565.33
4,067,813 A * 1/1978 Pielkenrood ....... B01D 21/0045
210/322

(Continued)

FOREIGN PATENT DOCUMENTS

| WO | 2009/003521 A1 | 1/2009 |
| WO | 2011/152788 A1 | 12/2011 |
| WO | 2014/016479 A1 | 1/2014 |

OTHER PUBLICATIONS

International Search Report and Written Opinion regarding International Application No. PCT/EP2015/065311, dated Oct. 9, 2015, 15 pages.

(Continued)

*Primary Examiner* — David A Rogers
(74) *Attorney, Agent, or Firm* — Eversheds Sutherland (US) LLP

(57) ABSTRACT

The invention discloses a flow control block for a stack of chromatography column modules, as well as a stack of chromatography modules comprising at least one flow control block. The flow control block is in a first position or configuration capable of connecting two chromatography column modules, or a chromatography column module and an endpiece, in parallel and in a second position or configuration it is capable of connecting two chromatography column modules, or a chromatography column module and an endpiece, in series.

32 Claims, 12 Drawing Sheets

(51) Int. Cl.
*G01N 30/02* (2006.01)
*G01N 30/88* (2006.01)
*B01D 15/18* (2006.01)

(52) U.S. Cl.
CPC ......... *G01N 30/6034* (2013.01); *G01N 30/88* (2013.01); *G01N 30/468* (2013.01); *G01N 2030/027* (2013.01); *G01N 2030/8881* (2013.01)

(56) References Cited

U.S. PATENT DOCUMENTS

| | | | | |
|---|---|---|---|---|
| 4,253,517 A * | 3/1981 | Timmerman | ........... | F01K 9/003 165/97 |
| 4,718,445 A * | 1/1988 | Lundberg | ........... | F16K 37/0008 116/201 |
| 5,251,670 A * | 10/1993 | Bates | ........... | F16K 11/0743 137/597 |
| 5,650,122 A * | 7/1997 | Harris | ........... | G01N 35/028 134/88 |
| 6,447,581 B2 * | 9/2002 | Gellert | ........... | G01N 30/32 96/102 |
| 6,550,497 B2 * | 4/2003 | Thiele | ........... | F16K 3/08 137/625.46 |
| 6,641,783 B1 * | 11/2003 | Pidgeon | ........... | G01N 30/20 210/656 |
| 6,845,968 B2 * | 1/2005 | Killeen | ........... | F15C 5/00 137/625.46 |
| 6,952,946 B2 * | 10/2005 | Mueller | ........... | G01N 30/78 73/23.4 |
| 7,003,948 B2 * | 2/2006 | Mares | ........... | B60K 17/10 60/424 |
| 7,015,465 B2 * | 3/2006 | Karol | ........... | G01N 30/466 210/198.2 |
| 7,108,789 B2 * | 9/2006 | Chiang | ........... | B01D 15/1857 210/192 |
| 7,137,286 B2 * | 11/2006 | Furukawa | ........... | G01N 30/20 73/23.42 |
| 7,361,281 B2 * | 4/2008 | Jensen | ........... | B01J 47/14 210/143 |
| 7,413,709 B2 * | 8/2008 | Roitman | ........... | B01J 19/0093 422/504 |
| 7,901,581 B2 * | 3/2011 | Bryntesson | ........... | B01D 15/1828 210/198.2 |
| 8,236,091 B2 * | 8/2012 | Yang | ........... | B01D 53/0423 134/1 |
| 8,347,688 B2 * | 1/2013 | O'Brien | ........... | G01N 1/2202 73/23.27 |
| 8,820,707 B2 * | 9/2014 | Chang | ........... | F16K 37/0008 251/216 |
| D716,416 S * | 10/2014 | Brown | ........... | D23/245 |
| 9,086,426 B2 * | 7/2015 | Liu | ........... | B01D 15/166 |
| 9,091,656 B2 * | 7/2015 | Lee | ........... | G01N 21/658 |
| 9,133,512 B2 * | 9/2015 | Cheng | ........... | C12Q 1/6872 |
| 9,341,604 B2 * | 5/2016 | Fan | ........... | G01N 30/463 |
| 9,347,020 B2 * | 5/2016 | Kelliher | ........... | B01D 15/185 |
| 9,683,974 B2 * | 6/2017 | Wang | ........... | G01N 30/30 |
| 2006/0118471 A1 | 6/2006 | Vidalinc | | |
| 2008/0092626 A1 * | 4/2008 | Lehmann | ........... | B01J 20/286 73/23.3 |
| 2008/0121017 A1 * | 5/2008 | Shah | ........... | G01N 30/88 73/23.42 |
| 2011/0232373 A1 | 9/2011 | Desmet et al. | | |
| 2013/0068671 A1 | 3/2013 | Gebauer et al. | | |
| 2013/0068977 A1 | 3/2013 | Picha et al. | | |

OTHER PUBLICATIONS

SE Search Report regarding SE Application No. 1450916-0, dated Feb. 27, 2015, 5 pages.

* cited by examiner a)

b)

a)

b)

STACKABLE CHROMATOGRAPHY COLUMN MODULES AND FLOW CONTROL BLOCKS

CROSS-REFERENCE TO RELATED APPLICATIONS

This application is a filing under 35 U.S.C. 371 of international application number PCT/EP2015/065311, filed Jul. 6, 2015, which claims priority to SE application number 1450916-0, filed Jul. 28, 2014, the entire disclosures of each of which are hereby incorporated by reference.

TECHNICAL FIELD OF THE INVENTION

The present invention relates to chromatography columns and in particular to chromatography column modules stackable with flow control blocks. The invention also relates to stacks of chromatography column modules interspersed with flow control blocks and to methods of assembling such stacks.

BACKGROUND OF THE INVENTION

The use of pre-packed stackable chromatography column modules or cartridges has a potential to increase flexibility in pilot and process scale bio-manufacturing. The flexibility arises from the ability to build a larger system for the required capacity and contaminant clearance from a number of standardized modules. However, a number of issues have to be addressed in order to provide such a system with full flexibility.

The binding capacity of the system depends on the bed volume and in order to increase capacity without affecting the back pressure at realistic residence times, it is desirable to be able to run chromatography column modules in parallel. On the other hand, for some separations a larger bed height may be required to achieve the required contaminant clearance. This leads to a need for serial coupling of chromatography column modules. Hence, it is desirable to have full flexibility with respect to serial and/or parallel coupling of the modules. It should be possible to provide an all parallel stack as well as an all serial stack and intermediate configurations, typically involving parallel coupling of several serial trains of chromatography column modules.

FR2681138 discloses a stack of chromatography column modules, but this construction requires a plurality of external tubing connections between the modules and is not suitable for large scale use. WO2011152788 also discloses a stack of chromatography column modules but does not provide details for the flexible connection of standardized modules in different configurations. These documents are hereby incorporated by reference in their entireties.

Accordingly there is a need for a chromatography column module system allowing flexible connection in parallel, serial and mixed mode operations without cumbersome external tubing connections. There is also a need for standardized components for assembling the system and for a convenient assembly method.

SUMMARY OF THE INVENTION

One aspect of the invention is to provide a flow control block allowing flexible connection of standardized chromatography column modules. This is achieved with a block as defined in the claims.

One advantage is that a single type of chromatography column module can be connected in different ways. Further advantages are that a high degree of scalability is achieved, a system of low footprint can be assembled, that no external tubing is needed within the system, convenient transport and storage of the components and that the formation of undesirable deadlegs in the system can be avoided.

A second aspect of the invention is to provide a standardized cost-efficient chromatography column module allowing flexible connection of module stacks interspersed with flow control blocks. This is achieved with a module as defined in the claims.

A third aspect of the invention is to provide a stack of chromatography column modules and flow control blocks. This is achieved with a stack as defined in the claims. The use of standardized modules and flow control blocks for the assembly of complex systems has the advantage that validation and verification is simplified. This applies in particular to sterile systems, which can be assembled from pre-sterilized components without having to validate the sterility of the assembled system.

A fourth aspect of the invention is to provide a method of assembling a stack of chromatography column modules and flow control blocks. This is achieved with a method as defined in the claims.

A fifth aspect of the invention is to provide use a stack of chromatography column modules and flow control blocks for separation of a biomolecule. This is achieved with the use as defined in the claims.

Further suitable embodiments of the invention are described in the dependent claims.

DRAWINGS

DETAILED DESCRIPTION OF EMBODIMENTS

Figure 1:
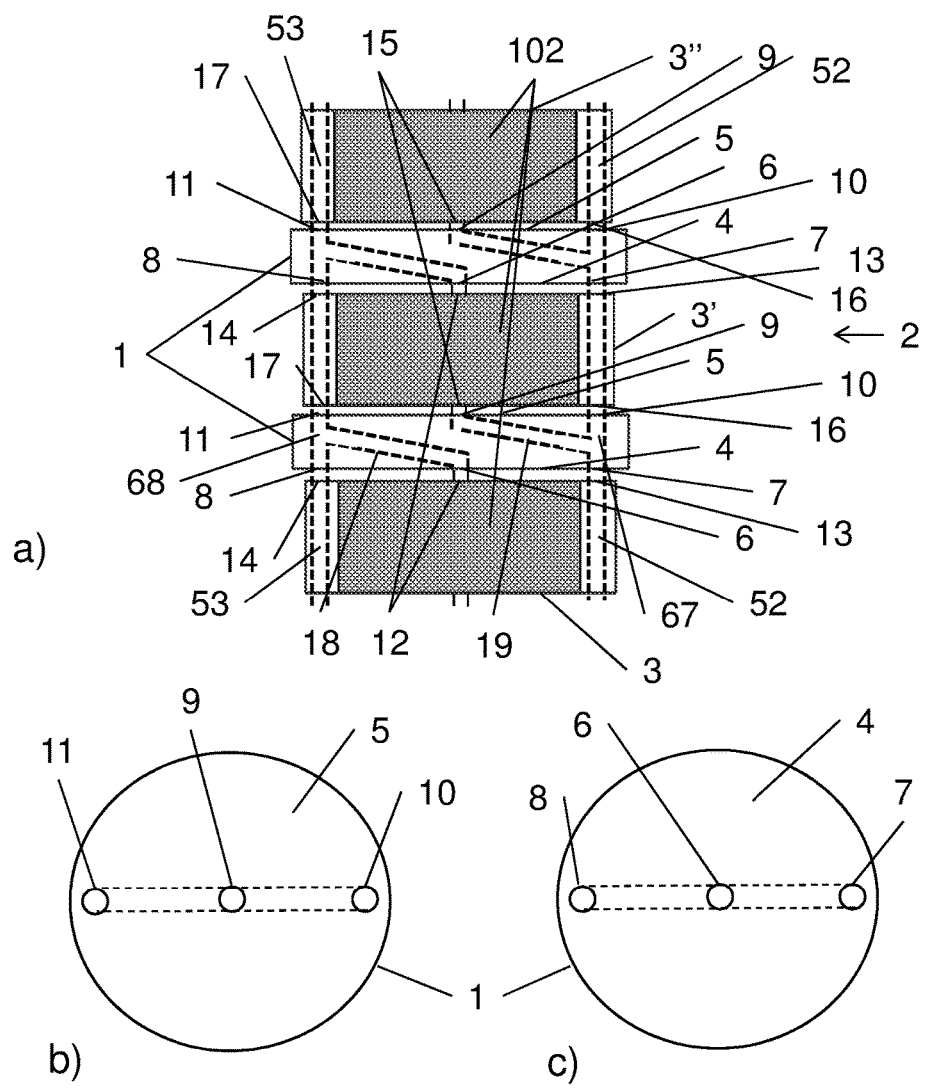
FIG. 1 shows a stack of flow control blocks and chromatography column modules according to the invention. a) a stack of three modules and 2 blocks (side view), b) top view of a block and c) bottom view of a block.

In one aspect, illustrated by FIGS. 1-12, the present invention discloses a flow control block 1;21;51;71;101; 121;151;221;271;371 for a stack 2;22;202 of chromatography column modules 3,3',3";23,23',23",23"';123, which is arranged to be moved or reconfigured between at least two out of a first, a second, a third and a fourth position or configuration. In the first position or configuration, alternatively called a (central) parallel flow position/configuration, the flow control block is capable of connecting either two chromatography column modules 3,3',3";23,23',23",23"', or a chromatography column module 23;23' and an endpiece 39;239, in parallel. The first position/configuration is particularly suitable for parallel connection of chromatography column modules inside the stack, i.e. for connections not involving the first or the last chromatography column module in the stack. In the second position or configuration, alternatively called a serial flow position/configuration, the block is capable of connecting two chromatography column modules 3,3',3";23,23',23", or a chromatography column module 23;23' and an endpiece 39;239, in series. In the third (exit side parallel flow) position or configuration, the flow control block is capable of parallel connection of two chromatography column modules, in particular at the exit end of a stack, such as the last and the penultimate chromatography column modules. In the fourth (feed side parallel flow) position or configuration, the flow control block is capable of parallel connection of two chromatography column modules, in particular at the feed end of a stack, such as the first and the second chromatography column modules.

In the drawings, the blocks, modules and stacks are all shown such that the flow direction is upwards, i.e. the inlet sides are at the bottom of the devices and the outlet sides are at the top. It is however equally possible to operate the stacks in downflow mode, provided that they are configured for this, e.g. by vertically flipping the structures shown in the drawings. When the terms first, last, feed end and exit end are used, they refer to the particular flow direction used, such that feed enters the stack at the feed end, and exits the stack at the exit end and the first module is the one closest to the feed end, while the last module is the one closest to the exit end.

In the different positions or configurations, the flow control block can be capable of fluidically connecting:
a) in the first position, a feed header outlet 13;43;113;173 of a first chromatography column module 3,3';23,23',23";103; 123;153 with a feed header inlet 7;46;116 and a bed inlet 15;45;115 of a second chromatography module 3',3";23', 23",23"';103, and a bed outlet 12;42;142;112;142 and an exit header outlet 14;44;114;144;174 of the first chromatography column module 3,3';23,23',23";103;123;153 with an exit header inlet 17;47;117 of the second chromatography column module;
b) in the second position, the bed outlet of the first chromatography column module with the bed inlet of the second chromatography column module;
c) in the third position, the feed header outlet of the first chromatography column module with the bed inlet of the second chromatography column module, and the bed outlet and the exit header outlet of the first chromatography column module with the exit header inlet of the second chromatography column module, and;
d) in the fourth position, the feed header outlet of the first chromatography column module with the feed header inlet and the bed inlet of the second chromatography column module, and the bed outlet of the first chromatography column module with the exit header inlet of the second chromatography column module.

In the third position or configuration, the block can be arranged to not allow fluidic connection between the feed header outlet 13;43;113;173 of the first chromatography column module 3,3';23,23',23";103;123;153 and the feed header inlet 7;46;116 of the second chromatography column module 3',3";23',23",23"';103 and in the fourth position or configuration, the block can be arranged to not allow fluidic connection between the exit header outlet 14;44;114;144; 174 of the first chromatography column module with the exit header inlet 17;47;117 of the second chromatography column module.

Figure 5:
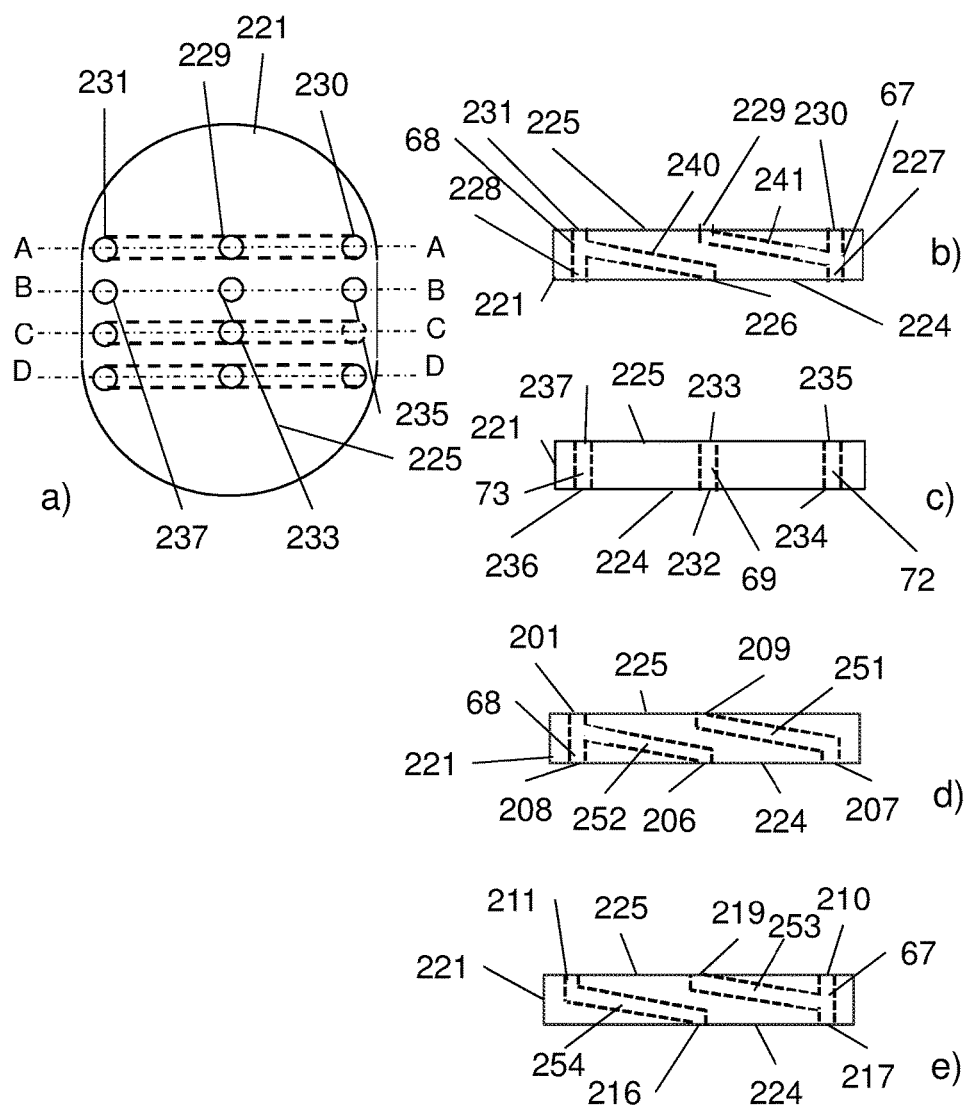
FIG. 5 shows details of the flow control block used in FIG. 3. a) top view of flow control block, b) section at A-A (central parallel flow part), c) section at B-B (serial flow part), d) section at C-C (exit side parallel flow part), e) section at D-D (feed side parallel flow part).
Figure 8:
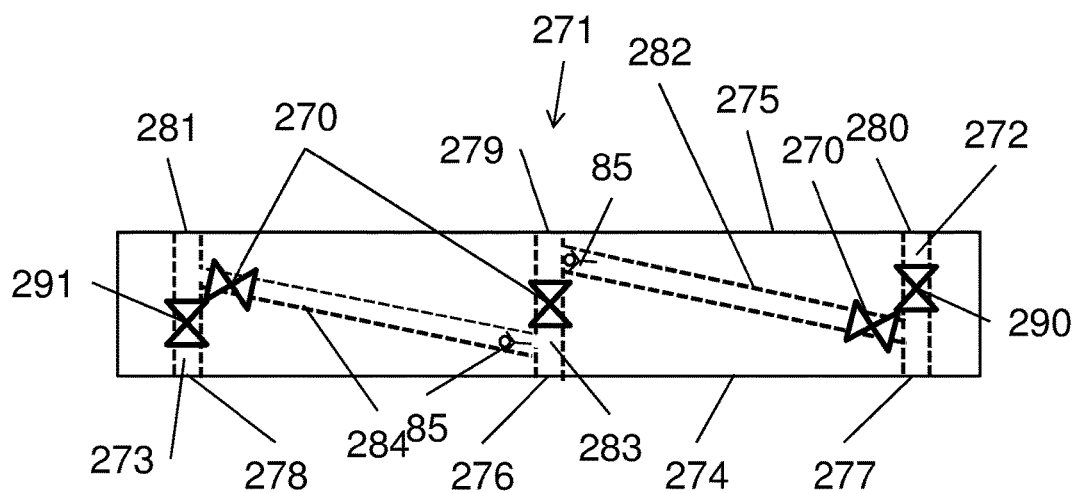
FIG. 8 shows two further flow control blocks of the invention with switch valve means. a) a reconfigurable between all four configurations and b) reconfigurable between the first, third and fourth configurations.
Figure 8:
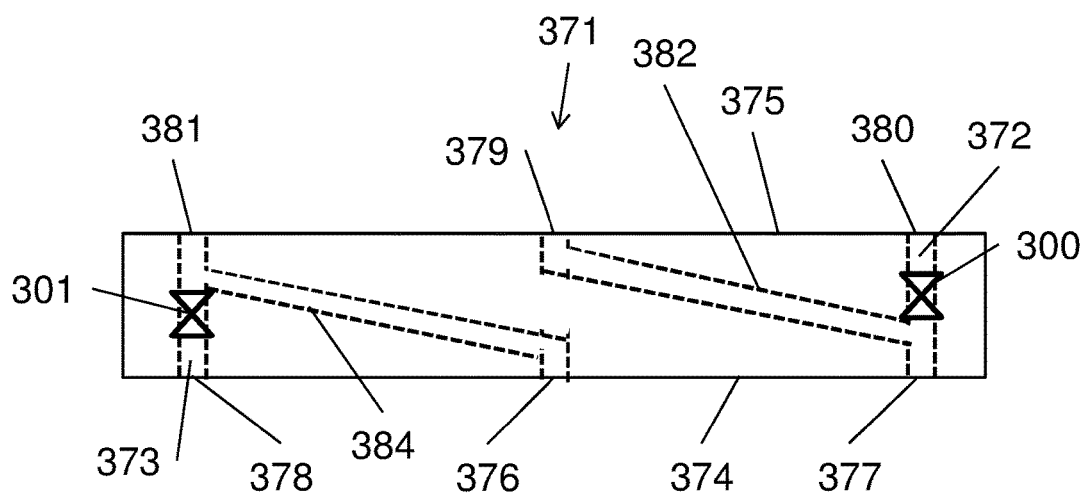

As illustrated in FIGS. 5 and 8, the flow control block 221;271 can be arranged to be moved or reconfigured between the first, the second, the third and the fourth positions or configurations. Alternatively, the flow control block 221;271;371 can be arranged to be moved or reconfigured between the first, the third and the fourth positions or configurations.

The block may have an inlet side 24;54;74;104;124;224; 274;374 with at least one bed inlet aperture 26,32;56;76; 106;126,132;206,216,226,232;276,376, at least one feed header inlet aperture 27,34;57;77;107;127,134;207,217,227, 234;277,377 and at least one exit header inlet aperture 28,36;58;78;108;128;208,238,236. On an outlet side 25;55; 75;105;125;225;275;375 the block may have at least one bed outlet aperture 29,33;59;79;109;129,133;209,219,229,233; 279;379, at least one feed header outlet aperture 30,35;60; 80;110;130,135;210,230,235 and at least one exit header outlet aperture 31,37;61;81;111;131,137;201,211,231;281; 381. The block may further have internal conduits 40,41; 62,63;64;69;82;84;140,141;240,241,251,252,253,254;282, 284;382,384 and header segments 67,68;72,73;272,273;372, 373 allowing fluidic connection in the first position or configuration i) between the feed header inlet aperture 27;57;77;107;127;227;277;377, the feed header outlet aperture 30;60;80;110;130;230;280;380 and the bed outlet aperture 29;59;79;109;129;229;279;379 and ii) between the bed inlet aperture 26;56;76;106;126;226;276;376, the exit header inlet aperture 28;58;78;108;128;228;278;378 and the exit header outlet aperture 31;61;81;111;131;231;281;381. In the first position/configuration, the bed inlet and bed outlet apertures are suitably not fluidically connected to each other. In the second position or configuration, a bed inlet aperture 32;56;76;106;132;232;276 can be fluidically connected with a bed outlet aperture 33;59;79;109;133;233;279 via a bed conduit 63;69;283, and if desired, a feed header inlet aperture 34;57;77;107;134;234;277 may be connected with a feed header outlet aperture 35;60;80;110;135;235;280 via a feed header segment 67;72;272 and an exit header inlet aperture 36;58;78;108;136;236;278 may be connected with an exit header outlet aperture 37;61;81;111;137;237;281 via an exit header segment 68;73;273. The bed conduit, the feed header segment and the exit header segment are suitably not fluidically connected to each other in this position/configuration. In the third position or configuration, a feed header inlet aperture 207;277;377 can be fluidically connected with a bed outlet aperture 209;279;379 and both of a bed inlet aperture 206;276;376 and an exit header inlet aperture 208;278;378 can be fluidically connected to an exit header outlet aperture 201;281;381. The bed inlet and bed outlet apertures are suitably not fluidically connected to each other and the feed header inlet aperture is suitably not fluidically connected to any feed header outlet aperture. This is suitable to avoid any deadleg formation in the feed header segment of the last chromatography column module during parallel operation. In the fourth position or configuration, a feed header inlet aperture 217; 277;377 can be fluidically connected to both a bed outlet aperture 219;279;379 and a feed header outlet aperture 210;280;380, while a bed inlet aperture 216;276;376 can be fluidically connected to an exit header outlet aperture. In this position/configuration, the bed inlet and bed outlet apertures are suitably not fluidically connected to each other and the exit header outlet aperture is suitably not fluidically connected to any exit header inlet aperture. This is suitable to avoid any deadleg formation in the exit header segment of the first chromatography column module during parallel operation.

The block can have a generally cylindrical or prismatic shape with e.g. 5-100 cm (circle-equivalent) diameter and the inlet and outlet sides can be generally planar, optionally with protruding connector parts and, when applicable, corresponding recesses to accommodate such parts. The block can also be an open frame structure with conduits and apertures placed inside a supporting frame, e.g. a circular or prismatic frame forming an outer perimeter or mantle of the block. The inlet and outlet sides can suitably be parallel and the height of the block (distance between inlet and outlet side) can be e.g. 1-20 cm, such as 2-10 cm. The internal conduits and header segments may form channels in an otherwise solid or mainly solid block, but the block can equally well have an open internal structure, with conduits and/or header segments formed e.g. by lengths of tubing or molded parts.

Figure 2:
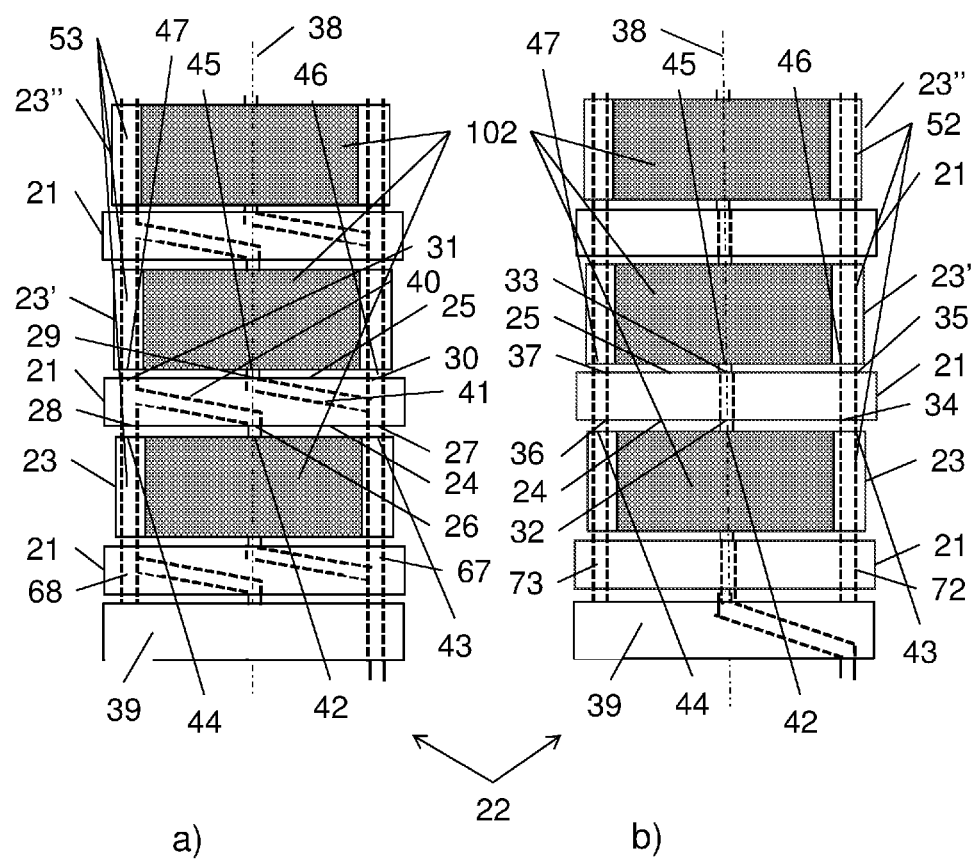
FIG. 2 shows a stack of flow control blocks and chromatography column modules according to the invention. a) side view of a stack with all the flow control blocks arranged for parallel flow, b) side view of a stack with all the flow control blocks arranged for serial flow.
Figure 3:
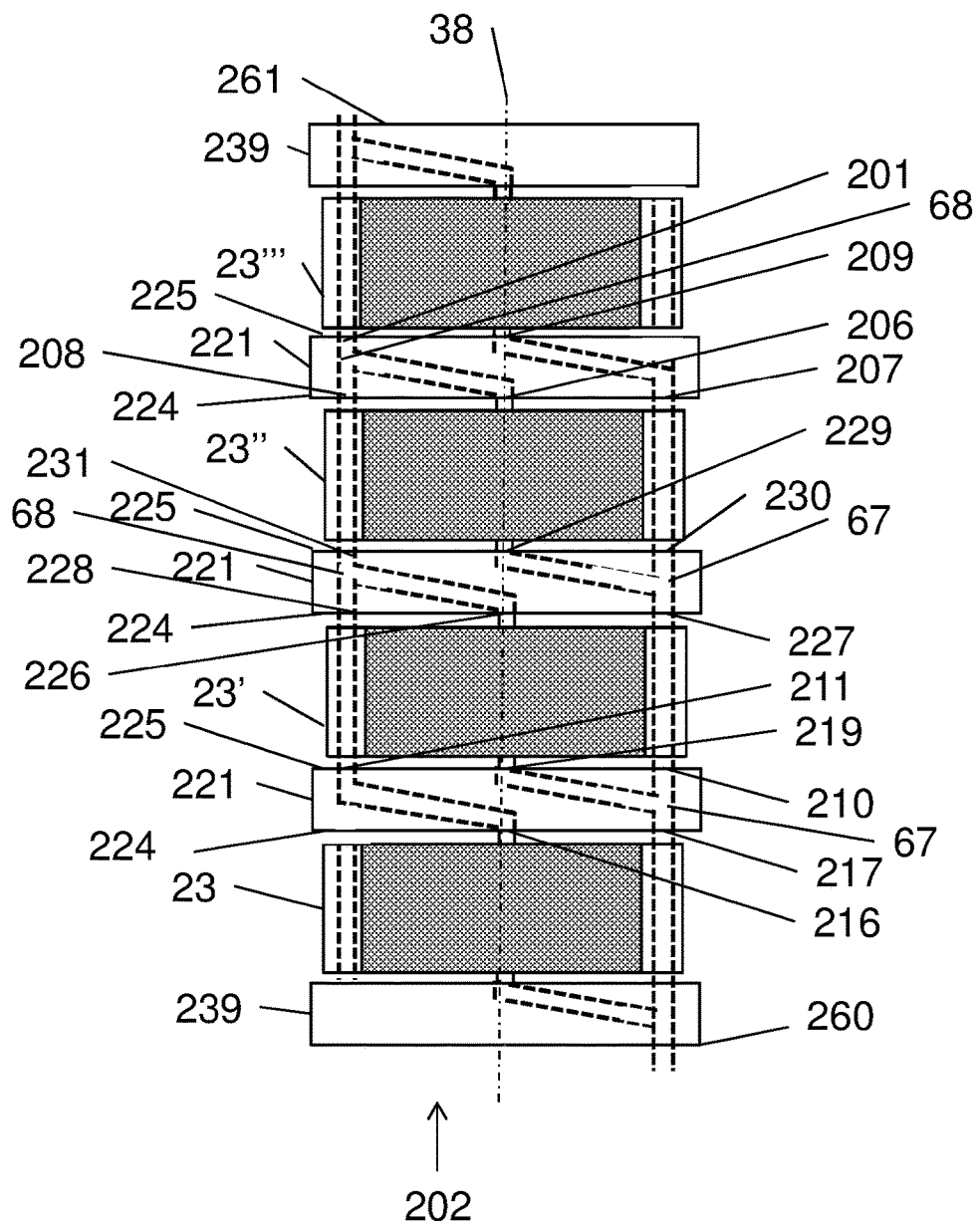
FIG. 3 shows a stack of flow control blocks and chromatography column modules according to the invention, with the flow control blocks arranged for parallel flow.
Figure 4:
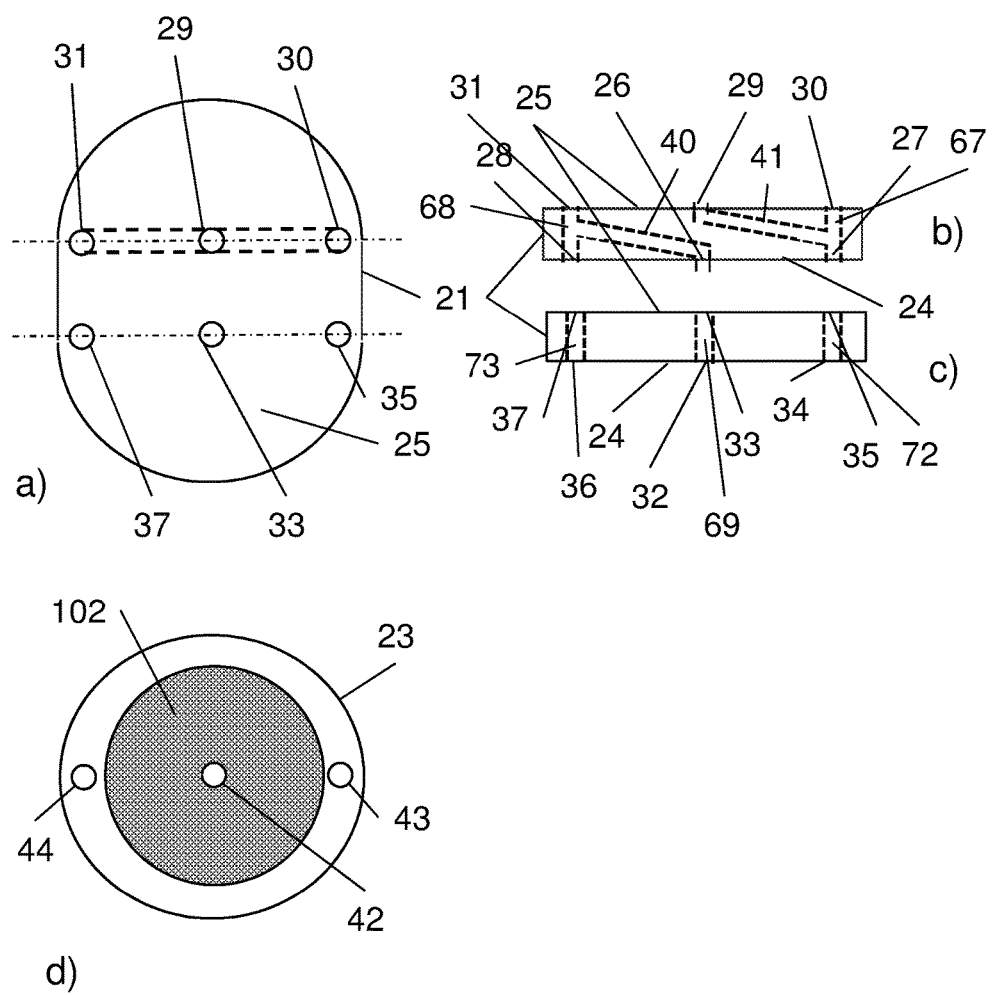
FIG. 4 shows details of the flow control block and chromatography column modules used in FIG. 2. a) top view of flow control block, b) section through the parallel flow part of the block, c) section through the serial flow part of the block, d) top view of chromatography column module.
Figure 6:
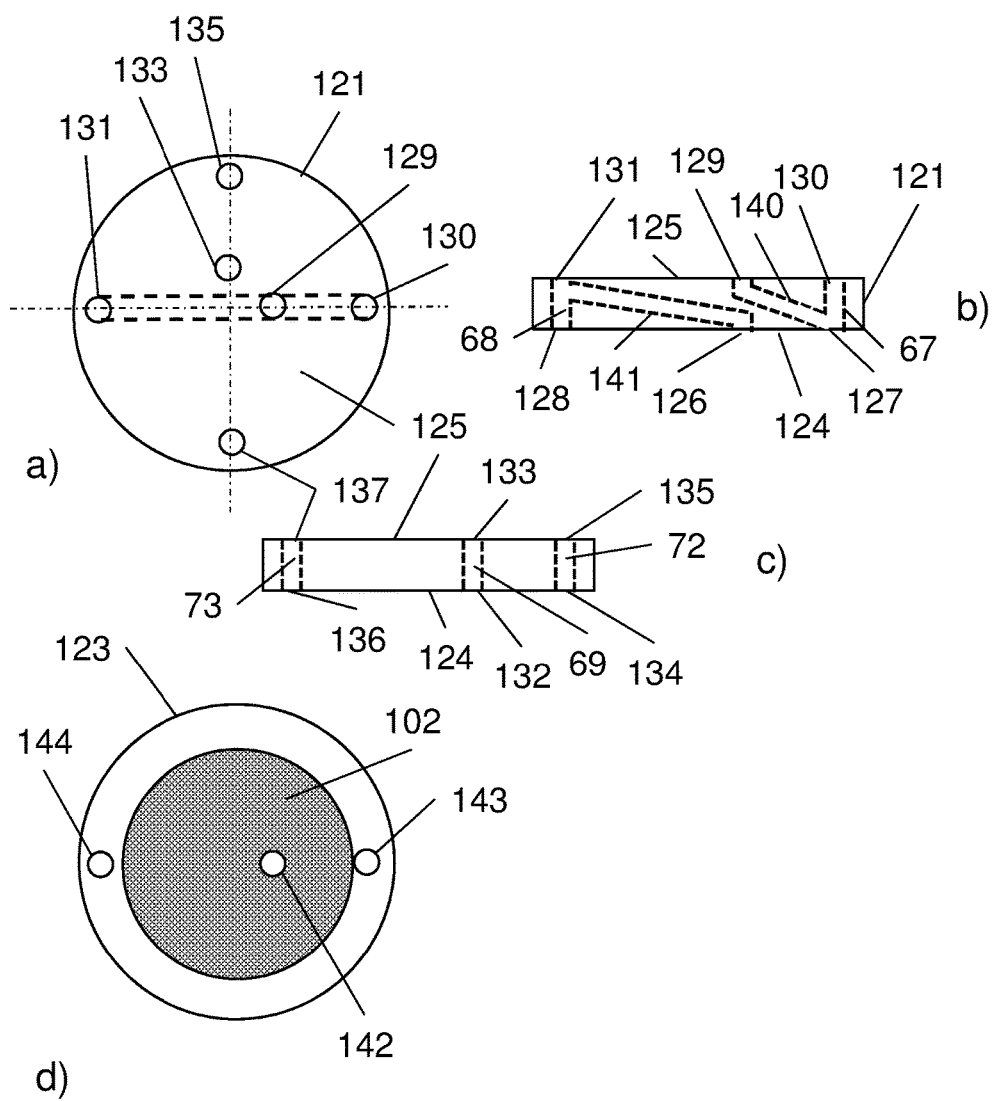
FIG. 6 shows details of alternative flow control blocks and chromatography column modules for use in the stack of FIG. 2. a) top view of flow control block, b) section through the parallel flow part of the block, c) section through the serial flow part of the block, d) top view of chromatography column module.
Figure 12:
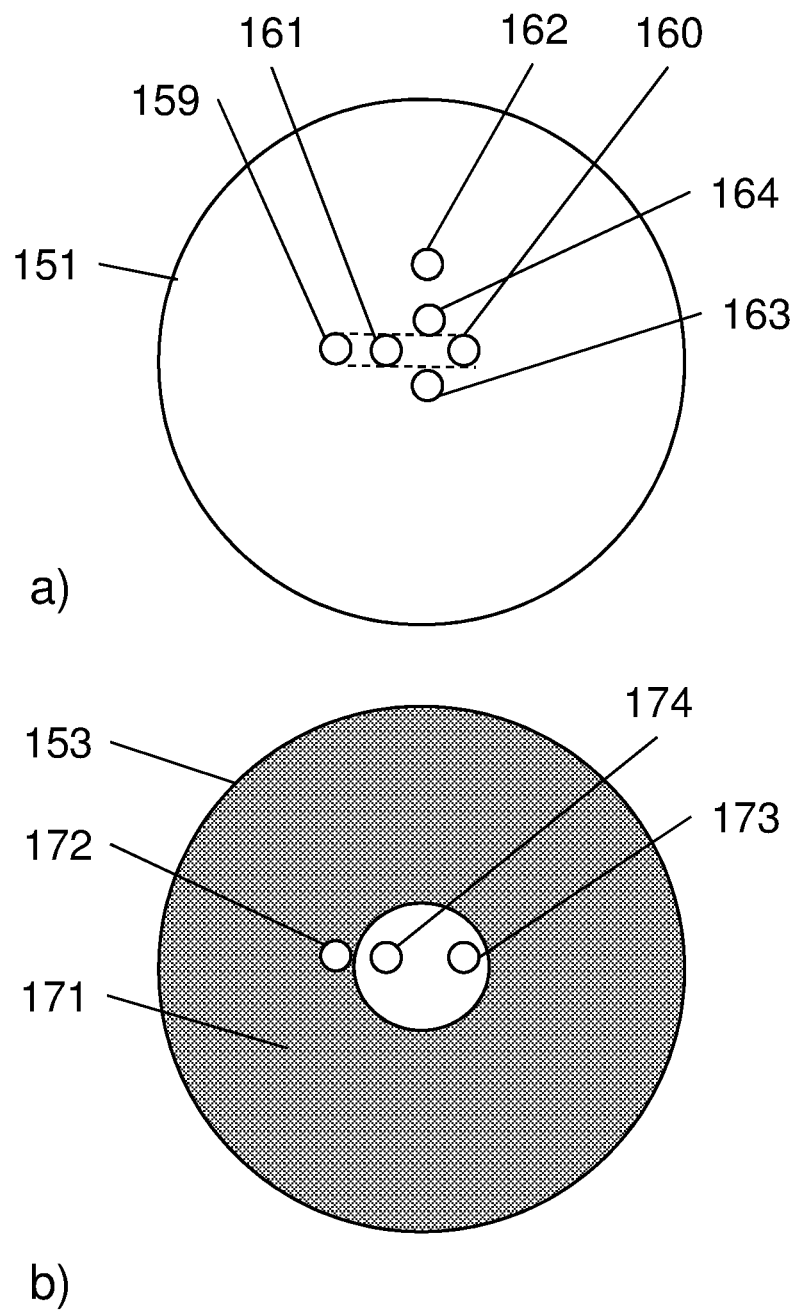
FIG. 12 shows a chromatography column module and a flow control block according to the invention. a) top view of flow control block, b) top view of chromatography column module.

In certain embodiments, illustrated by FIGS. 2, 4-6 and 12, the block 21;121;151;221 is moveable between the different positions by translational and/or or rotational movement in relation to a chromatography column module 23,23',23'',23''';123 or an endpiece 39. The movement can suitably be in a direction essentially orthogonal to a length axis 38 of the chromatography column module or stack of chromatography column modules, as indicated in FIGS. 2 and 3. Alternatively, a rotational movement can be made by flipping the block vertically. The movement can be purely translational, as indicated in FIGS. 4 and 5 for blocks 21,221, purely rotational, as indicated in FIGS. 6 and 12 for blocks 121 and 151, or a combination of translational and rotational movement. An advantage of having a movable block is that simple constructions without any moving parts can be used. A further advantage is that it can be easy to see the position of a block, particularly in conjunction with a visual indicator on the block as discussed below.

The flow control block 21;121;151;221 may, as illustrated in FIGS. 4-6 and 12, comprise at least two sets of apertures and internal conduits, selected from:

a) a first set of apertures 26,27,28,29,30,31;126,127,128, 129,130,131;159,160,161; 226,227,228,229,230,231 and internal conduits 40,41,67,68;140,141;240,241 adapted to fluidically connect two chromatography column modules when the block is in the first position;

b) a second set of apertures 32,33;34,35,36,37;132,133,134, 135,316,137;232,233,234, 235,236,237 and internal conduits 69,72,73 adapted to fluidically connect two chromatography column modules when the block is in the second position;

c) a third set of apertures 201,206,207,208,209 and internal conduits 68,251,252 adapted to fluidically connect two chromatography column modules when the block is in the third position, and;

d) a fourth set of apertures 210,211,216,217,219 and internal conduits 67,253,254 adapted to fluidically connect two chromatography column modules when the block is in the fourth position.

The sets of apertures and internal conduits can be independent of each other, i.e. the apertures and conduits of one set are not fluidically connected to those of any other set. Alternatively, for a block arranged to be moveable only between the first, third and fourth positions by rotation, the bed inlet and the bed outlet apertures (which are not connected to each other in any of these positions) may be common for all three positions and located at the center (the axis of rotation).

Block 21;121;151;221 can comprise an inlet side 24;124 and an outlet side 25;125;224 and at least two sets of apertures and internal conduits, selected from:

a) a first set of apertures and internal conduits comprising on the inlet side a first bed inlet aperture 26;126;226, a first feed header inlet aperture 27;127;227 and a first exit header inlet aperture 28;128;228 and on the outlet side a first bed outlet aperture 29;129;229, a first feed header outlet aperture 30;130;230 and a first exit header outlet aperture 31;131;231. The first bed inlet aperture 26;126;226 and the first bed outlet aperture 29;129;229 are suitably not fluidically connected with each other.

The first bed inlet aperture 26;126;226 and the first exit header inlet aperture 28;128;228 can be fluidically connected or connectable with the first exit header outlet aperture 31;131;231 via an internal conduit 40;140;240 and the first feed header inlet aperture 27;127;227 can be fluidically connected or connectable with the first bed outlet aperture 29;129;229 and with the first feed header outlet aperture 30;130;230 via an internal conduit 41;141;241, and;

b) a second set of apertures and internal conduits comprising a second (serial) bed inlet aperture 32;132;232 on the inlet side, which is fluidically connected or connectable with a second (serial) bed outlet aperture 33;133;233 on the outlet side and, optionally, a second (serial) feed header inlet aperture 34;134;234 on the inlet side, which is fluidically connected or connectable with a second (serial) feed header outlet aperture 35;135;235 on the outlet side and a second (serial) exit header inlet aperture 36;136;236 on the inlet side fluidically connected or connectable with a second (serial) exit header outlet aperture 37;137;237 on the outlet side.

c) a third set of apertures and internal conduits comprising on the inlet side a third bed inlet aperture 206, a third feed header inlet aperture 207 and a third exit header inlet aperture 208 and on the outlet side a third bed outlet aperture 209 and a third exit header outlet aperture 201. The third bed inlet aperture 206 and the third exit header inlet aperture 208 can be fluidically connected or connectable with the third exit header outlet aperture 201 via an internal conduit 252 and the third feed header inlet aperture 207 can be fluidically connected or connectable with the third bed outlet aperture 209 via an internal conduit 251.

d) a fourth set of apertures and internal conduits comprising on the inlet side a fourth bed inlet aperture 216 and a fourth feed header inlet aperture 217, and on the outlet side a fourth bed outlet aperture 219, a fourth feed header outlet aperture 210 and a fourth exit header outlet aperture 211. The fourth bed inlet aperture 216 can be fluidically connected or connectable with said fourth exit header outlet aperture 211 via an internal conduit 254 and the fourth feed header inlet aperture 217 can be fluidically connected or connectable with the fourth bed outlet aperture 219 and the fourth feed header outlet aperture 210 via an internal conduit 253.

In some embodiments of the moveable block, illustrated by FIGS. 2-5 and 12, in the different positions the apertures are arranged to be in register with inlets and outlets of chromatography column modules according to:

a) In the first (parallel) position the first bed inlet, first feed header inlet and first exit header inlet apertures 26,27,28; 126,127,128;226,227,228 of the block can all be arranged to be in register with a bed outlet 42;142, a feed header outlet 43;143 and an exit header outlet 44;144 of a first chromatography column module 23,23',23";123 to be mounted on the inlet side of the block. Further, the first bed outlet, first feed header outlet and first exit header outlet apertures 29,30,31;129,130,131;229,230,231 of the block may be arranged to be in register with a bed inlet 45, a feed header inlet 46 and an exit header inlet 47 of a second chromatography column module 23',23",23";123 to be mounted on the outlet side of the block.

b) In the second position the second (serial) bed inlet aperture 32;132;232 can be arranged to be in register with the bed outlet 42;142 of the first chromatography column module and the second (serial) bed outlet aperture 33;133;233 can be arranged to be in register with the bed inlet 45 of the second chromatography column module. The second (serial) feed header inlet and second (serial) exit header inlet apertures 34,36;134,136;234,236 of the block may also be arranged to be in register with the feed and exit header outlets 43,44;143,144 of the first chromatography column module and the second feed header outlet and second exit header outlet apertures 35,37;135,137;235,237 may be arranged to be in register with the feed and exit header inlets 46,47 of the second chromatography column module.

c) In the third position the third bed inlet, third feed header inlet and third exit header inlet apertures 206,207,208 can be arranged to be in register with a bed outlet 42;142, a feed header outlet 43;143 and an exit header outlet 44;144 of a first chromatography column module 23;123 and the third bed outlet and third exit header outlet apertures 201,209 can be arranged to be in register with a bed inlet 45, a feed header inlet 46 and an exit header inlet 47 of a second chromatography column module 23'.

d) In the fourth position the fourth bed inlet and fourth feed header inlet apertures 216,217 can be arranged to be in register with a bed outlet 42;142, a feed header outlet 43;143 and an exit header outlet 44;144 of a first chromatography column module 23;123. The fourth bed outlet, fourth feed header outlet and fourth exit header outlet apertures 219, 210,211 can be arranged to be in register with a bed inlet 45, a feed header inlet 46 and an exit header inlet 47 of a second chromatography column module 23'.

The connection between the apertures of the block and the inlets and outlets of the chromatography column modules can be made simply by clamping the stack together, in which case gaskets may be used to ensure sealing, but connection can also be achieved by connectors as described below.

Figure 7:
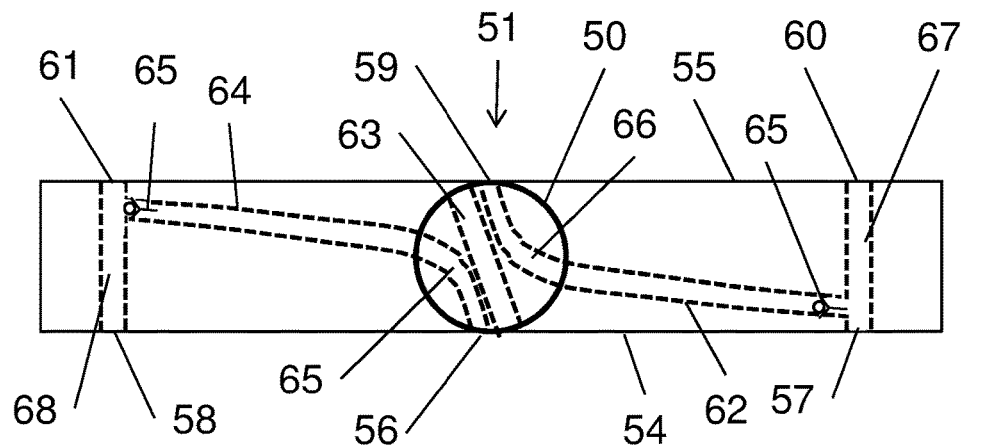
FIG. 7 shows details of two flow control blocks of the invention with switch valve means. a) a rotary valve and b) a plurality of valves.
Figure 7:
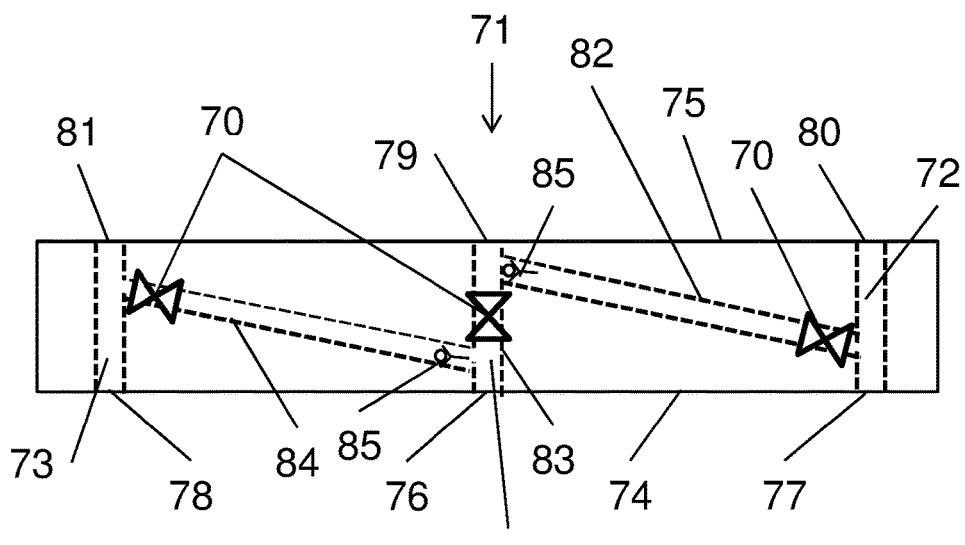
Figure 11:
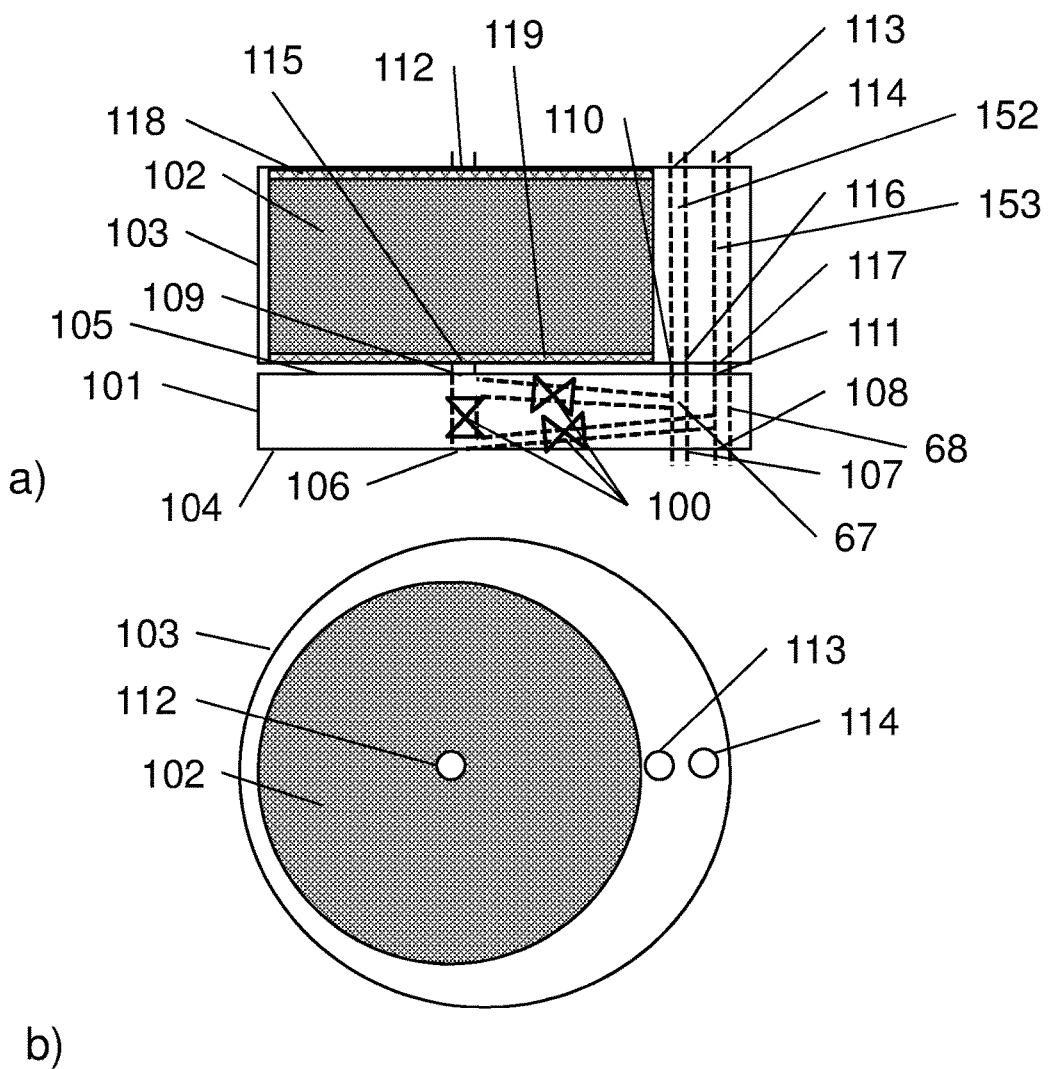
FIG. 11 shows a chromatography column module and a flow control block according to the invention. a) side view, b) top view of chromatography column module.

In certain embodiments, illustrated by FIGS. 7-8 and 11, the block 51;71;101;271;371 is adapted to be reconfigured between the different configurations by operation of a switch valve means 50;70;100;270,290,291;300,301, which can suitably be integrated in the block. The switch valve means can e.g. be one or more valves, which is/are arranged to close (and open) the fluidic connections between the feed header inlet aperture 57;77;107;277 and the bed outlet aperture 59;79;109;279 and between the bed inlet aperture 56;76;106;276 and the exit header outlet aperture 61;81;111; 281. The switch valve means is then also arranged to open (and close) a fluidic connection between the bed inlet aperture 56;76;106;276 and the bed outlet aperture 59;79; 109;279. These arrangements are useful for reconfiguration between either of the first, third and fourth configurations and the second configuration.

As illustrated in FIG. 8, in some embodiments, the switch valve means 270,290,291;300,301 may additionally or alternatively comprise valves 290,291;300,301 adapted to close either the conduit 272;372 between a feed header inlet aperture 277;377 and a feed header outlet aperture 280;380 or the conduit 273;373 between an exit header inlet aperture 278;378 and an exit header outlet aperture 281;381. These arrangements are useful for reconfiguration between the first, third and fourth configurations.

In some embodiments of the block with the switch valve means (FIGS. 7-8 and 11), the block comprises an inlet side 54;74;104;274;374 and an outlet side 55;75;105;275;375, with a bed inlet aperture 56;76;106;276;376, a feed header inlet aperture 57;77;107;277;377 and an exit header inlet aperture 58;78;108;278;378 on the inlet side and a bed outlet aperture 59;79;109;279;379, a feed header outlet aperture 60;80;110;280;380 and an exit header outlet aperture 61;81; 111;281;381 on the outlet side. The switch valve means 50;70;100;270,290,291;300,301 can be moveable between at least two of a first (central parallel) valve position, a second (serial) valve position, a third (exit side parallel) valve position and a fourth (feed side parallel) valve position.

In the first valve position the bed inlet aperture 56;76; 106;276;376 and the exit header inlet aperture 58;78;108; 278;378 are fluidically connected with the exit header outlet aperture 61;81;111;281;381 and the feed header inlet aperture 57;77;107;277;377 is fluidically connected with the bed outlet aperture 59;79;109;279;379 and the feed header outlet aperture 60;80;110;280;380.

In the second valve position the bed inlet aperture 56;76; 106;276 is fluidically connected with the bed outlet aperture 59;79;109;279.

In the third valve position the bed inlet aperture 276;376 and the exit header inlet aperture 278;378 are fluidically connected with the exit header outlet aperture 281;381 and the feed header inlet aperture 277;377 is fluidically connected with the bed outlet aperture 279;379, such as only with the bed outlet aperture.

In the fourth valve position the bed inlet aperture 276;376 is fluidically connected with the exit header outlet aperture 281;381, such as only with the exit header outlet aperture, and the feed header inlet aperture 277;377 is fluidically connected with the bed outlet aperture 279;379 and the feed header outlet aperture 280;380.

The bed outlet aperture 59;79;109;279;379 and the bed inlet aperture 56;76;106;276;376 are suitably not fluidically connected to each other when the switch valve means 50;70;100;270,290,291;300,301 is in the first, third or fourth valve position.

In certain embodiments, illustrated by FIG. 7a), the switch valve means comprises a rotary valve 50. This can e.g. be a multichannel rotary valve as depicted in FIG. 5a, which is capable of moving from a first (parallel) position where the bed inlet aperture 56 is fluidically connected with exit header inlet aperture 58 and exit header outlet aperture 61 via internal conduit 64 and exit header section 68 and the feed header inlet aperture 57 is fluidically connected to the bed outlet aperture 59 and feed header outlet aperture 60 via internal conduit 62 and feed header segment 77 to a second (serial) position where the bed inlet aperture 56 is connected to the bed outlet aperture 59 via bed conduit 63. In addition to the rotary valve, the block may also comprise check valves, e.g. check valves 65, which prevent the formation of deadlegs in conduits 62 and 64 when the valve is in the second position.

In some embodiments, illustrated by FIGS. 7 b) and 8, the switch valve means comprises a plurality of valves 70;100; 270,290,291;300,301 which are arranged to close and open at least two of the internal conduits 82,83,84;272,273,282, 283,284;372,373 in the block 71;101;271;371. The valves can suitably be located in, or in direct connection with, the internal conduits and can be operated such that in the first (parallel) position any bed conduit 83;283 is closed while conduits 82;282;382 (feed conduit) and 84;284;384 (exit conduit) are open, as are conduits 272,273;372,373. In the second (serial) position bed conduit 83;283 and conduits 272,273;372,373 are open while conduits 82;282 and 84;284 are closed. In the third position any bed conduit 283 is closed while conduits 282;382 and 284;384 are open and conduit 272;372 is closed. In the fourth position, any bed conduit 283 is closed while conduits 282;382 and 284;384 are open and conduit 273;373 is closed. The block may further comprise check valves, e.g. check valves 85, which prevent the formation of deadlegs in conduits 82 and 84 when the switch valve means is in the second position.

As discussed above, the block may comprise one or more check valves 65;85 (FIG. 7). These can have the function of closing off certain conduits to avoid the formation of deadlegs which are undesirable form a sanitary point of view and also increase the hold-up volume. However, check valves may also be introduced for other purposes as well. They can e.g. be used to eliminate back flow between chromatography column modules and they can be used to prevent draining of liquid-filled chromatography column modules during assembly of the stack.

In certain embodiments, the block comprises a visual indicator showing whether the block is in the first or second position or configuration. This indicator allows easy verification of the parallel vs serial configuration of the stack. In the movable blocks 21;121;151;221 of FIGS. 2,4-6 and 12, the indicator can e.g. be a coloured marking on the side of the block which shows the position of the block, e.g. as an outline of the actual flowpath(s) through the stack. In the valve controlled blocks 51;71;101 of FIGS. 5 and 8, the indicator can e.g. be a marked external valve handle in combination with a marking on the side of the block.

Figure 9:
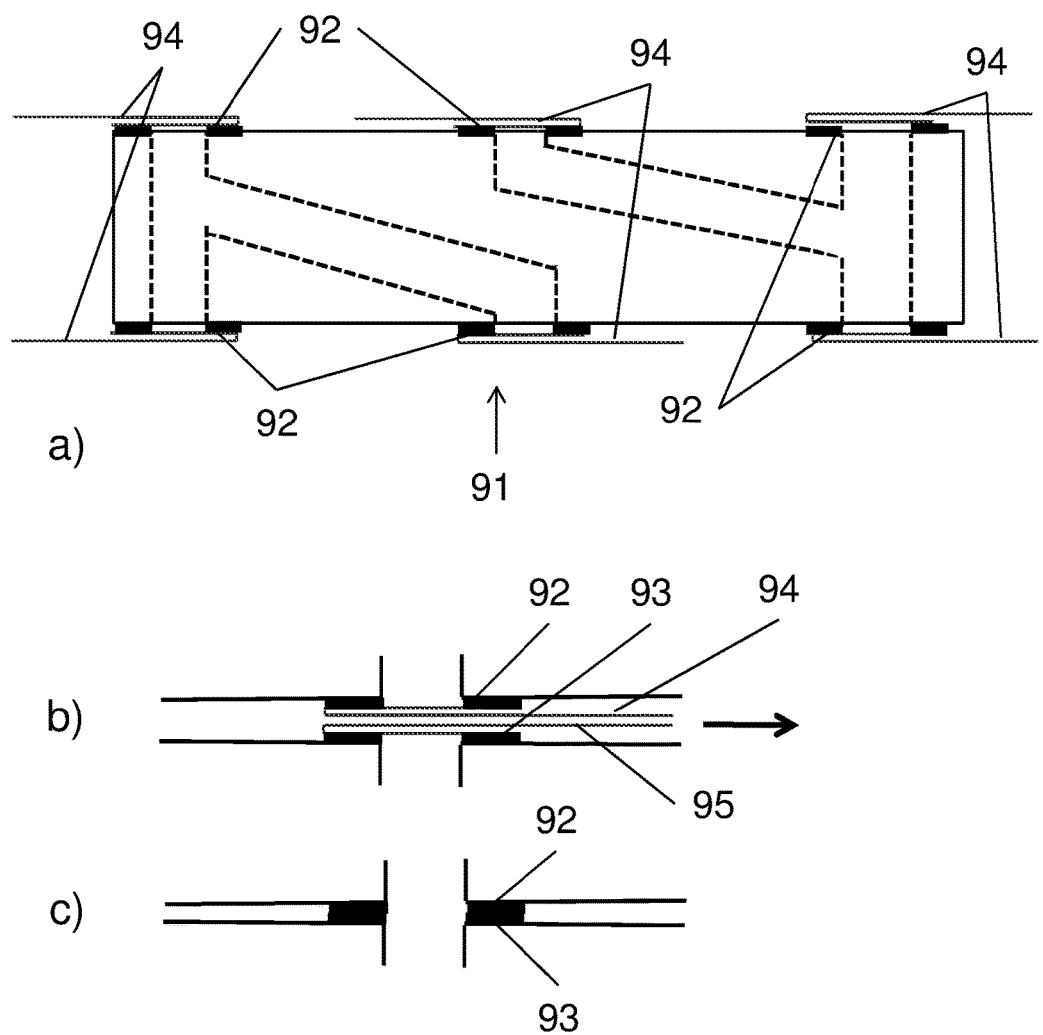
FIG. 9 shows details of a flow control block of the invention with sanitary connectors. a) block, b) connectors during assembly, c) connectors after assembly.

In some embodiments, illustrated by FIG. 9, each of the bed inlet, feed header inlet, exit header inlet, bed outlet, feed header outlet and exit header outlet apertures comprises a connector 92, arranged to engage a connector 93 in a corresponding bed outlet, feed header outlet, exit header outlet, bed inlet, feed header inlet and exit header inlet of one or more chromatography column modules when mounted together with said one or more chromatography column modules in a stack. These connectors may e.g. be aseptic connectors, comprising a folded over protective film 94 arranged to be pulled out together with a corresponding film 95 in an abutting connector 93 on a chromatography column module or an endpiece. The films may be common for several connectors or each connector may have its own film. The connectors may also include fasteners to ensure the permanency of the connection, e.g. as disclosed in U.S. Pat. No. 6,679,529, WO 2009/002468 and WO 2013/147688, which are hereby incorporated by reference in their entireties. The use of connectors with fasteners allows connection of the stack without clamping. The use of aseptic connectors means that presterilized, e.g. gamma radiation sterilized, blocks, modules and endpieces can be assembled in a non-sterile environment without compromising the sterility of the stack and with no need of verifying the sterility of the assembly.

The block may comprise a vent valve in the feed header segment and if desired also in the exit header segment. This facilitates venting of air from the feed (and exit) header during set up of the stack.

Figure 10:
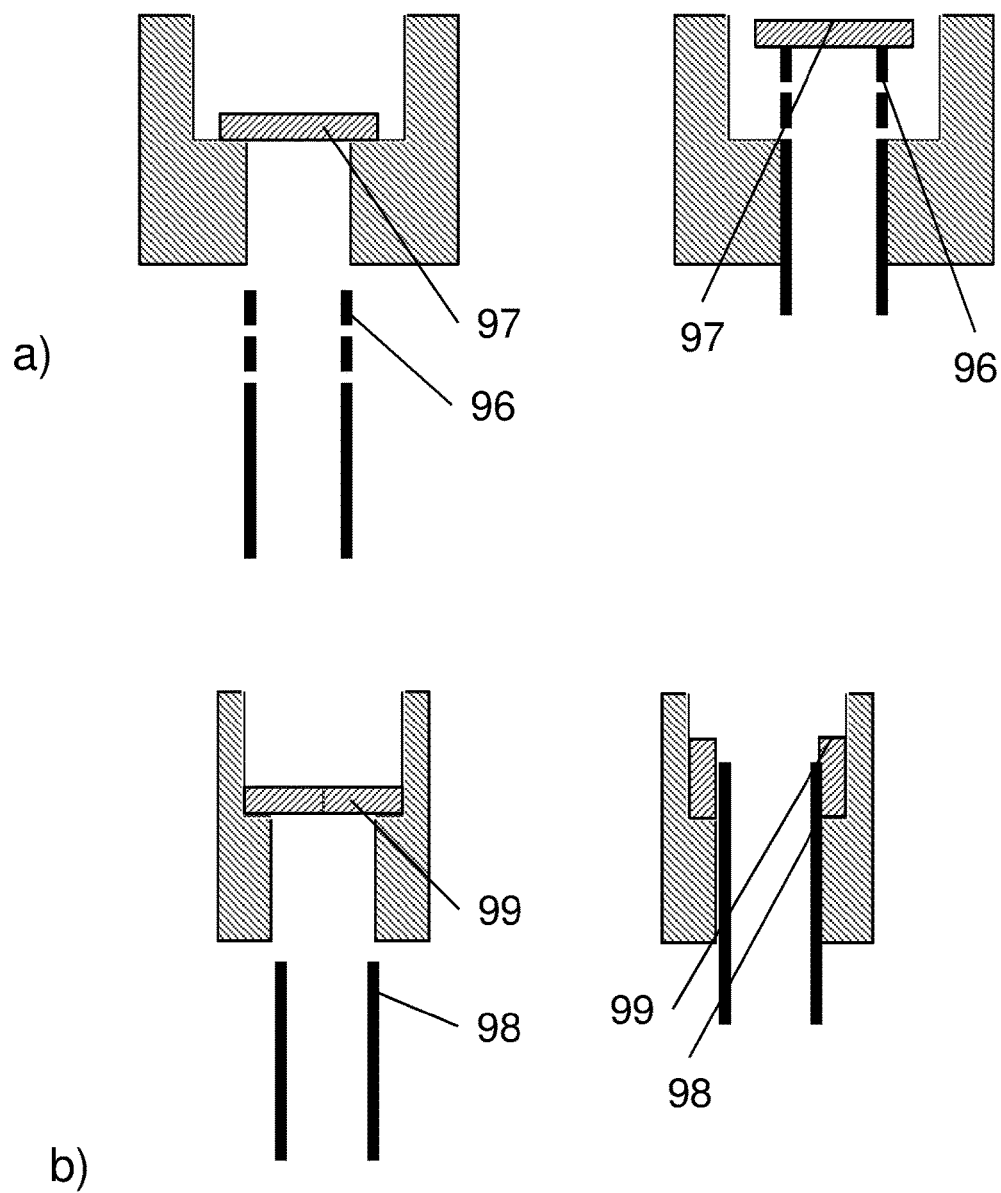
FIG. 10 shows details of valves for use in the inlets and outlets of the chromatography column modules of the invention, as well as valve opening means for use in the flow control blocks of the invention. a) one valve embodiment before and after assembly, b) an alternative valve embodiment before and after assembly.

In certain embodiments, illustrated by FIG. 10, each of the bed inlet, feed header inlet, exit header inlet, bed outlet, feed header outlet and exit header outlet apertures comprises a valve opening member 96;98. The valve opening member is arranged to open a valve 97;99 in a corresponding bed outlet, feed header outlet, exit header outlet, bed inlet, feed header inlet and exit header inlet of one or more chromatography column modules when mounted together with the flow control block in a stack. The use in the inlets and outlets of valves operable by valve opening members has the advantage that draining of liquid-filled chromatography column modules during assembly of the stack can be prevented.

In one aspect, illustrated by FIGS. 1-12, the present invention discloses a flow control block 1;21;51;71;101; 121;151;221;271;371 for a stack 2;22;202 of chromatography column modules 3,3',3";23,23',23",23''', where the flow control block comprises an inlet side 4;24;54;74;104;124; 224;274;374 and an outlet side 5;25;55;75;105;125;225; 275;375. The inlet side has a bed inlet aperture 6;26;56;76; 106;126;226;276;376, a feed header inlet aperture 7;27;57; 77;107;127;227;277;377 and optionally an exit header inlet aperture 8;28;58;78;108;128;228;278;378, while the outlet side has a bed outlet aperture 9;29;59;79;109;129;229;279; 379, an optional feed header outlet aperture 10;30;60;80; 110;130;230;280;380 and an exit header outlet aperture 11;31;61;81;111;131;231;281;381. The bed inlet aperture and optionally the exit header inlet aperture are fluidically connected or connectable with the exit header outlet aperture via an internal conduit 18;40;64;84;141;240;284;384 and the feed header inlet aperture is fluidically connected or connectable with the bed outlet aperture and optionally the feed header outlet aperture via an internal conduit 19;41; 62;82;140;241;282;382. The bed inlet aperture can be located opposite the bed outlet aperture, the feed header inlet aperture can be located opposite the feed header outlet aperture and the exit header inlet aperture can be located opposite the exit header outlet aperture.

In some embodiments, the bed inlet, feed header inlet and exit header inlet apertures are arranged to be in register with a bed outlet 12;42;112;142;172, a feed header outlet 13;43; 113;143;173 and an exit header outlet 14;44;114;144;174 respectively of a first chromatography column module 3,3'; 23,23',23";103;123;153 and the bed outlet, feed header outlet and exit header outlet apertures are arranged to be in register with a bed inlet 15;45;115, a feed header inlet 16;46;116 and an exit header inlet 17;47;117 respectively of a second chromatography column module 3',3";23',23",23'"; 103.

In certain embodiments, the block 51;71;101;271;371 further comprises a switch valve means 50;70;100;270, which in a first (parallel flow) position provides fluidic connection between the bed inlet aperture and the exit header outlet aperture and between the feed header inlet aperture and the bed outlet aperture, and which in a second (serial flow) position provides fluidic connection between the bed inlet aperture and the bed outlet aperture and between the feed header inlet aperture and the exit header outlet aperture.

In some embodiments, the block further comprises one or more check valves 65;85, as discussed above.

In a second aspect, illustrated by FIGS. 1-6 and 11-12, the invention discloses a chromatography column module 3;23; 103;123;153 stackable with like chromatography column modules and at least two flow control blocks 1;21;51;71; 101;121;151;221;371, suitably with the flow control blocks directly connected to the chromatography column module. The chromatography column module comprises a bed 102; 171, a bed inlet 15;45;115, a bed outlet 12;42;112;142;172, a feed header section 52;152 with a feed header inlet 16;46;116 and a feed header outlet 13;43;113;143;173 and an exit header section 53;153 with an exit header inlet 17;47;117 and an exit header outlet 14;44;114;144;174. The bed outlet and the feed header outlet are arranged to be in register with the bed inlet and feed header inlet apertures of a first flow control block 1;21;51;71;101;121;151;221;371 as described above and the bed inlet and the exit header inlet are arranged to be in register with the bed outlet and exit header outlet apertures of a second flow control block as described above.

In certain embodiments of the chromatography column module 3;23;103;123;153, the bed 102;171 has a cylindrical or annular shape. A cylindrical shape, as shown in FIGS. 1-4, 6 and 11, provides for easy distribution of liquid over the bed from a central or near central bed inlet. An annular shape, as shown in FIG. 12, allows for a convenient placing of header segments and other conduits inside the hollow lumen of the annular bed. The diameter of the bed may e.g. be 5-100 cm and the bed height e.g. 1-50 cm. The bed can be composed of any chromatography media known in the art, e.g. a packed bed of porous particles such as ion exchange resins, multimodal resins, affinity resins, hydrophobic interaction chromatography resins, reversed phase chromatography resins or hydroxyapatite. The bed can also be a porous monolith, a stack of adsorptive membranes or a depth filter medium. Packed beds of porous particles are particularly contemplated.

In some embodiments, illustrated by FIG. 11, the chromatography column module 103 further comprises two distributors 118,119. One distributor 119 is located between the bed inlet 115 and the bed 102, while the other distributor 118 is located between the bed 102 and the bed outlet 112. The distributors provide efficient distribution of liquid from the bed inlet over the bed area and correspondingly efficient collection of liquid from the bed area to the bed outlet. The distributors can be designed according to principles well known in the art of chromatography columns.

In certain embodiments of the chromatography column module, illustrated by FIG. 10, each of the bed outlet, feed header outlet, exit header outlet, bed inlet, feed header inlet and exit header inlet comprises a valve 97;99, arranged to be in a closed position until the chromatography column module is mounted together with at least one flow control block equipped with valve opening members 96;98 as disclosed above. The use in the inlets and outlets of valves operable by valve opening members has the advantage that draining of liquid-filled chromatography column modules during assembly of the stack can be prevented. Alternatively, draining can be prevented by check valves in the chromatography column modules.

In a third aspect, illustrated by FIGS. 1-3, the present invention discloses a stack of chromatography column modules, comprising at least two chromatography column modules as described above, fluidically connected by at least one flow control block as described above. The flow control block can be arranged to provide flow of a fluid through said chromatography column modules in parallel, but it can also be arranged to provide flow through the modules in series or in mixed parallel/serial flow, e.g. as a serial train of several parallel parts of the stack. As both the chromatography column modules and the flow control blocks contain feed header segments and exit header segments, the stack will have a complete feed header and exit header when the segments are placed in register with each other. This allows for convenient parallel operation. The stack may further comprise one or two endpieces, preferably one endpiece at each end of the stack. The endpieces can be connected to the chromatography column modules via flow control blocks as described above or they can alternatively be directly connected to chromatography column modules.

In certain embodiments, illustrated by FIG. 3, the stack comprises at least four chromatography column modules 23,23',23",23'" and at least three flow control blocks 221, with the flow control block closest to a feed end 260 of the stack being in the fourth position or configuration, the flow control block closest to an exit end 261 of the stack being in the third position or configuration and the remaining flow control blocks being in the first or second position or configuration, such as in the first position or configuration.

In some embodiments, the flow resistance through each chromatography column module is substantially the same, such as with less than 10%, less than 5% or less than 2% difference. This is to ensure that the flow rate through modules connected in parallel is substantially the same. To achieve this, the chromatography column modules can be prepared according to the methods described in WO2011078772A1 or U.S. patent application Ser. No. 14/201,175, which are hereby incorporated by reference in their entireties, and which allow the preparation of modules with substantially identical flow resistance. Further, the stack can suitably be constructed such that the total flow resistances of the flowpaths inside the stack are substantially identical for all parallel chromatography column modules. Likewise, the stack can be constructed such that the hold-up volume of the flowpath for each parallel chromatography is substantially the same. This is e.g. the case for the stack depicted in FIG. 3 with the same hold-up volume in the flowpaths through each module.

In a fourth aspect the present invention discloses a method of assembling a stack of chromatography column modules as described above, said method comprising the steps of:
a) arranging a series of chromatography column modules interspersed with flow control blocks;
b) optionally configuring the flow control blocks in the first and/or second configuration as desired, and;
c) connecting and mounting the chromatography column modules and flow control blocks into a stack.

In a fifth aspect the present invention discloses use of the stack as described above for separation of a biomolecule. The biomolecule can be e.g. a protein (e.g. an immunoglobulin), a peptide, a virus or a nucleic acid to be used as a biopharmaceutical. The biomolecule may be present in a crude feed, e.g. a clarified cell broth or in a semi-purified form, e.g. recovered from a previous chromatography step. The separation may involve clearance of impurities or contaminants such as host cell proteins, viruses, endotoxins or aggregates, fragments, variants etc. of the biomolecule.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties as if individually incorporated.

The invention claimed is:

1. A flow control block for a stack of chromatography column modules, said flow control block in a first position or configuration being capable of connecting two chromatography column modules, or a chromatography column module and an endpiece, in parallel and in a second position or configuration being capable of connecting two chromatography column modules, or a chromatography column module and an endpiece, in series, wherein the flow control block is moveable between the different positions by translational or rotational movement in relation to a chromatography column module, such as in a direction essentially orthogonal to a length axis of said chromatography column module, said flow control block comprising at least two sets of apertures and internal conduits, selected from:
   a) a first set of apertures and internal conduits adapted to fluidically connect two chromatography column modules when the block is in the first position;
   b) a second set of apertures and internal conduits adapted to fluidically connect two chromatography column modules when the block is in the second position;
   c) a third set of apertures and internal conduits adapted to fluidically connect two chromatography column modules when the block is in the third position, and;
   d) a fourth set of apertures and internal conduits adapted to fluidically connect two chromatography column modules when the block is in the fourth position.

2. The flow control block of claim 1, comprising an inlet side and an outlet side and at least two sets of apertures and internal conduits, selected from:
   a) a first set of apertures and internal conduits comprising on the inlet side a first bed inlet aperture, a first feed header inlet aperture and a first exit header inlet aperture and on the outlet side a first bed outlet aperture, a first feed header outlet aperture and a first exit header outlet aperture, wherein said first bed inlet aperture and said first exit header inlet aperture are fluidically connected or connectable with said first exit header outlet aperture via an internal conduit and wherein said first feed header inlet aperture is fluidically connected or connectable with said first bed outlet aperture and said first feed header outlet aperture via an internal conduit;
   b) a second set of apertures and internal conduits comprising a second bed inlet aperture on the inlet side, fluidically connected or connectable with a second bed outlet aperture on the outlet side and, optionally, a second feed header inlet aperture on the inlet side fluidically connected or connectable with a second feed header outlet aperture on the outlet side and a second exit header inlet aperture on the inlet side fluidically connected or connectable with a second exit header outlet aperture on the outlet side;
   c) a third set of apertures and internal conduits comprising on the inlet side a third bed inlet aperture, a third feed header inlet aperture and a third exit header inlet aperture and on the outlet side a third bed outlet aperture and a third exit header outlet aperture, wherein said third bed inlet aperture and said third exit header inlet aperture are fluidically connected or connectable with said third exit header outlet aperture via an internal conduit and wherein said third feed header inlet aperture is fluidically connected or connectable with said third bed outlet aperture via an internal conduit, and;
   d) a fourth set of apertures and internal conduits comprising on the inlet side a fourth bed inlet aperture and a fourth feed header inlet aperture, and on the outlet side a fourth bed outlet aperture, a fourth feed header outlet aperture and a fourth exit header outlet aperture, wherein said fourth bed inlet aperture is fluidically connected or connectable with said fourth exit header outlet aperture via an internal conduit and wherein said fourth feed header inlet aperture is fluidically connected or connectable with said fourth bed outlet aperture and said fourth feed header outlet aperture via an internal conduit.

3. The flow control block of claim 2, wherein:
   a) in the first position said first bed inlet, first feed header inlet and first exit header inlet apertures are arranged to be in register with a bed outlet, a feed header outlet and an exit header outlet of a first chromatography column module and wherein said first bed outlet, first feed header outlet and first exit header outlet apertures are arranged to be in register with a bed inlet, a feed header inlet and an exit header inlet of a second chromatography column module;
   b) in the second position said second bed inlet aperture is arranged to be in register with the bed outlet of the first chromatography column module and said second bed outlet aperture is arranged to be in register with the bed inlet of the second chromatography column module and, optionally, said second feed header inlet and second exit header inlet apertures are arranged to be in register with the feed and exit header outlets of the first chromatography column module and said second feed header outlet and second exit header outlet apertures are arranged to be in register with the feed and exit header inlets of the second chromatography column module;
   c) in the third position said third bed inlet, third feed header inlet and third exit header inlet apertures are arranged to be in register with a bed outlet, a feed header outlet and an exit header outlet of a first chromatography column module and wherein said third bed outlet and third exit header outlet apertures are arranged to be in register with a bed inlet, a feed header inlet and an exit header inlet of a second chromatography column module, and/or;

d) in the fourth position said fourth bed inlet and fourth feed header inlet apertures are arranged to be in register with a bed outlet, a feed header outlet and an exit header outlet of a first chromatography column module and wherein said fourth bed outlet, fourth feed header outlet and fourth exit header outlet apertures are arranged to be in register with a bed inlet, a feed header inlet and an exit header inlet of a second chromatography column module.

4. The flow control block of claim 1, wherein the block is adapted to be reconfigured between the different configurations by operation of a switch valve means.

5. The flow control block of claim 4, wherein:
the block comprises an inlet side and an outlet side, the inlet side having a bed inlet aperture, a feed header inlet aperture and an exit header inlet aperture, the outlet side having a bed outlet aperture, a feed header outlet aperture and an exit header outlet aperture, and;
said switch valve means is moveable between a first valve position and a second valve position, wherein in the first valve position said bed inlet aperture and said exit header inlet aperture are fluidically connected with said exit header outlet aperture and said feed header inlet aperture is fluidically connected with said bed outlet aperture and said feed header outlet aperture and in the second valve position said bed inlet aperture is fluidically connected with said bed outlet aperture.

6. The flow control block of claim 5, wherein said bed outlet aperture and said bed inlet aperture are not fluidically connected to each other when the switch valve means is in the first valve position.

7. The flow control block of claim 6, wherein the switch valve means comprises valves adapted to close the conduit between a feed header inlet aperture and a feed header outlet aperture or the conduit between an exit header inlet aperture and an exit header outlet aperture.

8. The flow control block of claim 7, wherein said switch valve means comprises a rotary valve.

9. The flow control block of claim 7, wherein said switch valve means comprises a plurality of valves arranged to close and open at least two internal conduits.

10. The flow control block of claim 1, further comprising a visual indicator showing the position or configuration of the block.

11. The flow control block of claim 1, further comprising one or more check valves.

12. The flow control block of claim 1, wherein each of said bed inlet, feed header inlet, exit header inlet, bed outlet, feed header outlet and exit header outlet apertures comprises a connector, arranged to engage a connector in a corresponding bed outlet, feed header outlet, exit header outlet, bed inlet, feed header inlet and exit header inlet of one or more chromatography column modules when mounted together with said flow control block in a stack.

13. The flow control block of claim 12, wherein each of said connectors is a aseptic connector, comprising a folded over protective film arranged to be pulled out together with a corresponding film in an abutting connector.

14. The flow control block of claim 1, wherein each of said bed inlet, feed header inlet, exit header inlet, bed outlet, feed header outlet and exit header outlet apertures comprises a valve opening member, arranged to open a valve in a corresponding bed outlet, feed header outlet, exit header outlet, bed inlet, feed header inlet and exit header inlet of one or more chromatography column modules when mounted together with said one or more chromatography column modules in a stack.

15. A flow control block for a stack of chromatography column modules, said flow control block being arranged to be moved or reconfigured between at least two out of a first, a second, a third and a fourth position or configuration, wherein in the different positions or configurations, said flow control block is capable of capable of fluidically connecting:
a) in the first position, a feed header outlet of a first chromatography column module with a feed header inlet and a bed inlet of a second chromatography module, and a bed outlet and an exit header outlet of the first chromatography column module with an exit header inlet of the second chromatography column module;
b) in the second position, the bed outlet of the first chromatography column module with the bed inlet of the second chromatography column module;
c) in the third position, the feed header outlet of the first chromatography column module with the bed inlet of the second chromatography column module, and the bed outlet and the exit header outlet of the first chromatography column module with the exit header inlet of the second chromatography column module, and;
d) in the fourth position, the feed header outlet of the first chromatography column module with the feed header inlet and the bed inlet of the second chromatography column module, and the bed outlet of the first chromatography column module with the exit header inlet of the second chromatography column module,
wherein the control block is arranged to be moved or reconfigured between the first, the second, the third and the fourth positions or configurations.

16. The flow control block of claim 15, which is arranged to be moved or reconfigured between the first, the third and the fourth positions or configurations.

17. The flow control block of claim 16, wherein in the third position or configuration, the block does not allow fluidic connection between the feed header outlet of the first chromatography column module and the feed header inlet of the second chromatography column module and wherein in the fourth position or configuration, the block does not allow fluidic connection between the exit header outlet of the first chromatography column module with the exit header inlet of the second chromatography column module.

18. A flow control block for a stack of chromatography column modules, said flow control block comprising an inlet side and an outlet side, the inlet side having a bed inlet aperture, a feed header inlet aperture and an optional exit header inlet aperture, the outlet side having a bed outlet aperture, an optional feed header outlet aperture and an exit header outlet aperture, wherein said bed inlet aperture and optionally said exit header inlet aperture are fluidically connected or connectable with said exit header outlet aperture via an internal conduit and wherein said feed header inlet aperture is fluidically connected or connectable with said bed outlet aperture and optionally with said feed header outlet aperture via an internal conduit.

19. The flow control block of claim 18, wherein said bed inlet aperture is located opposite said bed outlet aperture, said feed header inlet aperture is located opposite said feed header outlet aperture and said exit header inlet aperture is located opposite said exit header outlet aperture.

20. The flow control block of claim 19, wherein said bed inlet, feed header inlet and optional exit header inlet apertures are arranged to be in register with a bed outlet, a feed header outlet and an exit header outlet respectively of a first chromatography column module and wherein said bed outlet, optional feed header outlet and exit header outlet apertures are arranged to be in register with a bed inlet, a feed header inlet and an exit header inlet respectively of a second chromatography column module.

21. The flow control block of claim 20, further comprising a switch valve means, which in a parallel flow (first) position provides fluidic connection between the bed inlet aperture and the exit header outlet aperture and between the feed header inlet aperture and the bed outlet aperture, and which in a serial flow (second) position provides fluidic connection between the bed inlet aperture and the bed outlet aperture and between the feed header inlet aperture and the exit header outlet aperture.

22. A chromatography column module stackable with like chromatography column modules and at least two flow control blocks, said chromatography column module comprising a bed, a bed inlet, a bed outlet, a feed header section with a feed header inlet and a feed header outlet and an exit header section with an exit header inlet and an exit header outlet, wherein said bed outlet and feed header outlet are arranged to be in register with the bed inlet and feed header inlet apertures of a first flow control block, and wherein said bed inlet and exit header inlet are arranged to be in register with the bed outlet and exit header outlet apertures of a second flow control block according to claim 1.

23. The chromatography column module of claim 22, wherein said bed has a cylindrical or annular shape.

24. The chromatography column module of claim 23, further comprising two distributors, one between said bed inlet and said bed, and one between said bed and said bed outlet.

25. The chromatography column module of claim 24, wherein each of said bed outlet, feed header outlet, exit header outlet, bed inlet, feed header inlet and exit header inlet comprises a valve, arranged to be in a closed position until the chromatography column module is mounted together with at least one flow control block.

26. A stack of chromatography column modules, comprising at least two chromatography column modules according to claim 25, fluidically connected by at least one flow control block.

27. The stack of claim 26, wherein said at least one flow control block is arranged to provide flow of a fluid through said chromatography column modules in parallel.

28. The stack of claim 27, wherein the flow resistance through each chromatography column module is substantially the same.

29. The stack of claim 28, further comprising one or two endpieces, optionally connected via a flow control block.

30. The stack of claim 29, comprising at least four chromatography column modules and at least three flow control blocks, with the flow control block closest to a feed end of the stack being in the fourth position or configuration, the flow control block closest to an exit end of the stack being in the third position or configuration and the remaining flow control blocks being in the first or second position or configuration, such as in the first position or configuration.

31. A method of assembling a stack of chromatography column modules according to claim 30, said method comprising the steps of:
   a) arranging a series of chromatography column modules interspersed with flow control blocks;
   b) optionally configuring the flow control blocks in the first and/or second configuration as desired, and;
   c) connecting and mounting the chromatography column modules and flow control blocks into a stack.

32. Use of the stack according to claim 30 for separation of a biomolecule.

* * * * *